United States Patent [19]

Finck et al.

[11] Patent Number: 4,675,294

[45] Date of Patent: Jun. 23, 1987

[54] PROCESS FOR PRODUCTION OF METHANE BY ANEROBIC FERMENTATION

[75] Inventors: Jean-Daniel Finck; Gérard Goma, both of Toulouse, France

[73] Assignee: Societe Nationale Elf Aquitaine, Courbevoie, France

[21] Appl. No.: 835,442

[22] Filed: Feb. 27, 1986

Related U.S. Application Data

[63] Continuation of Ser. No. 572,656, Jan. 20, 1984, abandoned.

[30] Foreign Application Priority Data

Jan. 20, 1983 [FR] France ................................. 83 00824

[51] Int. Cl.$^4$ ............................................... C12P 5/02
[52] U.S. Cl. .................................................. 435/167
[58] Field of Search ......................................... 435/167

[56] References Cited

U.S. PATENT DOCUMENTS 4,400,195  8/1983  Rijkens ................................ 435/167

FOREIGN PATENT DOCUMENTS 0114769  8/1984  European Pat. Off. ............ 435/167

OTHER PUBLICATIONS

Chemical Abstracts; vol. 98, (1983) #212616d; Japan. Biomass, vol. 2, (1982), pp. 43–55; Applied Science Publishers Ltd., Great Britain.

Primary Examiner—Jerome D. Goldberg
Assistant Examiner—Joseph A. Lipovsky
Attorney, Agent, or Firm—Burgess, Ryan & Wayne

[57] ABSTRACT

The invention has for an object a high-yield process for production of methane by anaerobic fermentation.

The process of the invention is characterized by the fact that from 0.001 to 0.35 millimoles per liter of an unsaturated fatty acid or of a derivative of this acid is added to the fermentation medium, employed under conventional fermentation conditions.

9 Claims, No Drawings

PROCESS FOR PRODUCTION OF METHANE BY ANEROBIC FERMENTATION

This application is a continuation of application Ser. No. 572,656, filed Jan. 20, 1984 now abandoned.

The present invention concerns a process for production of methane by anaerobic fermentation of organic substrates.

Processes of biogas production have been known for a number of years, and the fermentation operating conditions have been made the object of numerous researches. One of the major disadvantages of processes of this type is the low fermentation yield, due in part to the low rate of certain bacterial reactions. This low yield very often led users to employ reactors of large volume in order thus to increase the residence time of the substrate.

The invention has for a purpose to mitigate these shortcomings and to permit employing a biogas production process having improved yields.

The invention has for an object a process for methane production by anaerobic fermentation of organic substrates, employed under conventional fermentation conditions, characterized by the fact that at least one unsaturated fatty acid or a derivative of this acid is added to the fermentation medium in a concentration included between 0.001 and 0.35 millimoles per liter of the culture medium and such that, for the fatty acid considered, the biogas yield is at least equal to that obtained under the same conditions in the absence of the said fatty acid.

Preferably, in the process of the invention, alone or in a mixture, a fatty acid will be used having from 18 to 22 carbon atoms and at least two olefinic unsaturations per molecule.

The influence of unsaturated fatty acids having 18 carbon atoms on the production of methane has already been studied and been made the object of a publication by D. I. Demeyer and H. K, Henderickx in "Biochimica et Biophysica Acta", 137 (1967) pp. 484-497. It is clearly evident from the conclusions of this study that this type of acid is an inhibitor of methane production.

But with surprise it has been discovered that fatty acids or the derivatives of these acids such as esters can under certan conditions be strong activators of the production of methane by anaerobic fermentation of organic substrates.

For that, it is essential that the fatty acid be added to the culture medium in very low concentrations. These concentrations will generally be included between 0.001 and 0.35 millimoles per liter of culture medium. The optimal concentrations will vary within the range defined above according to the fatty acid employed in the process. For each fatty acid employed it will be necessary to verify that for the chosen concentration the biogas yield is at least equal to that obtained with a control culture without fatty acid ($R \geq 1$), R being the ratio of the volumes of biogas produced experimentally (Vex) and in the control test ($V_t$).

Naturally, the fatty acid or its derivative will have to be soluble in the culture medium; if it is not, it will then be preferable to emulsify it previously to the addition.

Among the fatty acids or their derivatives which can be used by preference in the process of the invention, one can cite by way of example:
linoleic acid
linolenic acid
arachidonic acid
clupanodonic acid
ricinoleic acid
esters of these acids
mixtures of these acids such as linseed oil.

When linoleic acid or linseed oil will be used as the fatty acid, it will be particularly advantageous to add a concentration included between 0.10 and 0.25 mM per liter (mM being the abbreviation for millimole).

In the case where linolenic acid or its derivatives is chosen, it is essential to use it in a lower concentration, included between 0.001 and 0.1 mM per liter. Beyond this concentration the biogas yield drops considerably ($R<1$).

The process of the invention is illustrated by Examples 1 to 32 described below.

EXAMPLES 1 to 29

The study of the production of biogas by fermentation of a substrate constituted of cattle manure set to contain 10% of dry matter has been conducted batchwise with various fatty acids in different concentrations, this too under identical operating conditions. The fermentation is accomplished at 35° C. at an average initial pH of 7.4 in unstirred glass bottles. Fermentations are conducted generally for 30 days and, in certain cases, limited to 8 days. The criterion for comparison of the yields is the production of biogas by comparison with that from a control test (Ex 1), without acid, it being specified that the methane content of the biogas is equal to 55% and identical in all of these experiments.

The specified operating conditions and the results obtained are indicated in Table 1 below.

Analysis of Table 1 shows that:
saturated fatty acids are totally inactive;
monoethylenic fatty acids are weakly active (Examples 6 to 9);
diethylenic and triethylenic fatty acids are particularly active (Examples 10 to 12 and 14 to 16 respectively); they become inactive and even inhibitors when their concentration is too large (Examples 13 and 17). It is to be remarked that linolenic acid is very active at low concentration and becomes an inhibitor at a not very high concentration;
linseed oil is active, and this activity increases in the course of time (Examples 21 to 23);
the gains in yield are extremely large, here exceeding 200%.

EXAMPLES 30 to 32

Comparison Experiments have been conducted in a 5 m³ continuous pilot plant under the following experimental conditions, the feeding of the reactor being carried out 5 days per week:

| | |
|---|---|
| Temperature | 35° C. |
| pH | 6.8-7.3 |
| Average charging rate | 6.7 kg volatile solids/m³ · d |
| Theoretical average residence time | 17.4 d |
| Average nature of the charge: | |
| total dry matter (TDM) | 13.86% by weight |
| volatile solids | 80.7% TDM |
| cellulose | 17.15% TDM |
| hemicelluloses | 18.2% TDM |
| lignin | 14.1% TDM |
| total nitrogen | 1.92% TDM |

The results obtained without fatty acid (Ex 30), with 0.027 mM/L of the monolinolenate of Examples 25 to 29 (Ex 31), and 0.054 mM of this monolinolenate (Ex 32) are summarized in Table 2 below.

The process of the invention can be used for treating any suitable fermentable substrate and in particular substrates rich in cellulose and/or lignocellulose.

The substrate can be of animal origin, for example manures, or effluents from slaughter-houses; it can also be of vegetable origin, for example crop wastes such as alfalfa, Jerusalem artichoke, sugar cane, corn, etc; finally it can be of industrial origin and constituted from for example effluents from dairies, canneries, the paper industry, and the like.

TABLE 1

| Ex | Added product | Nature of the fatty acid* | Concentration mM/L | Biogas production after 8 d | Biogas production after 30 d |
|----|---------------|---------------------------|--------------------|-----------------------------|------------------------------|
| 1  | Control       | —                         | —                  | 100                         | 100                          |
| 2  | Capric acid   | $C_{10}$ saturated        | 0.35               | 100.7                       | —                            |
| 3  | Myristoleic acid | $C_{14 I}$             | 0.13               | 96                          | —                            |
| 4  | Stearic acid  | $C_{18}$ saturated        | 0.09               | 98                          | —                            |
| 5  |               |                           | 0.21               | 96.5                        |                              |
| 6  | Oleic acid    | $C_{18 I}$                | 0.07               | 110                         | 106                          |
| 7  |               |                           | 0.14               | 110                         | 103.5                        |
| 8  |               |                           | 0.21               | 102.5                       | 102.5                        |
| 9  |               |                           | 0.53               | 105                         | 103.5                        |
| 10 | Linoleic acid | $C_{18 II}$               | 0.07               | 142                         | 127.5                        |
| 11 |               |                           | 0.14               | 206                         | 209                          |
| 12 |               |                           | 0.21               | 237                         | 222                          |
| 13 |               |                           | 0.53               | 37.7                        | 23                           |
| 14 | Linolenic acid | $C_{1 III}$              | 0.017              | 162                         | 141                          |
|    |               |                           | 0.035              | 162                         | 160.5                        |
|    |               |                           | 0.09               | 227                         | 217                          |
|    |               |                           | 0.18               | 47.1                        | 29                           |
| 18 | Ricinoleic acid | $C_{18}$ OH             | 0.2                | 91                          | —                            |
| 19 | Arachidonic acid | $C_{20 IV}$            | 0.08               | 111                         | —                            |
| 20 | Clupanodonic acid | $C_{22 V}$            | 0.06               | 125                         | —                            |
| 21 | Linseed oil   | $C_{18 I}$ 18%            | 0.07               | 107.5                       | 133                          |
| 22 |               | $C_{18 II}$ 19%           | 0.14               | 88                          | 207                          |
| 23 |               | $C_{18 III}$ 51%          | 0.21               | 168                         | 272.5                        |
| 24 |               | Others 12%                | 0.53               | 22                          | 10                           |
| 25 | Unsaturated   | Monolinolenate            | 0.027              | —                           | —                            |
| 26 | fatty acid    | of hydroxy-               | 0.054              | —                           | —                            |
| 27 | ester         | propylene                 | 0.13               | 117                         | 114                          |
| 28 |               | glycol                    | 0.37               | 100                         | 110                          |
| 29 |               |                           | 0.52               | 37.5                        | 8                            |

*The Roman numeral index specifies the number of olefinic double bonds in the molecule ($C_{18 III}$ = an acid with 18 carbon atoms with three olefinic unsaturations).

TABLE 2

| Examples | 30 | 31 | 32 |
|----------|----|----|----|
| Crude biogas productivity ($m^3/m^3 \cdot$ day) | 1.76 | 2.50 | 2.31 |
| Methane content (%) | 55 | 55 | 55 |
| Yield by comparison with the control (%) | 100 | 142 | 131.5 |
| Content of monolinolenate (mM/L) | 0 | 0.027 | 0.054 |

We claim:

1. In a process for production of biogas containing methane by anaerobic fermentation, under conventional fermentation conditions, of a fermentation medium comprised of an organic substrate of animal, vegetable or industrial origin, said medium being rich in at least one of cellulose, hemicellulose or lignocellulose, the improvement which comprises adding to said fermentation medium, between 0.001 and 0.35 millimoles per liter of fermentation medium, of at least one unsaturated fatty acid or ester thereof, wherein said fatty acid is selected from the group consisting of:
linoleic acid,
linolenic acid,
arachidonic acid,
clupanodonic acid,
acids from linseed oil, esters of said acids and mixtures of said acids and wherein the yield of said biogas containing methane is at least 114% of that obtained without said fatty acid after a fermentation period of 30 days.

2. The process of claim 1 wherein said fatty acid is emulsified prior to adding to said fermentation medium.

3. The process of claim 1 wherein the yield of methane is up to about 272.5 percent of that obtained without said fatty acid.

4. A process according to claim 1 wherein the fatty acid is linolenic acid.

5. A process according to claim 4, wherein the fatty acid is an ester of linolenic acid.

6. The process of claim 4 wherein the concentration of said fatty acid is between 0.001 and 0.1 mM/L.

7. A process according to any one of claim 4 through 5, wherein the concentration of fatty acid is between 0.001 and 0.10 mM/L.

8. A process according to claim 1 wherein the fatty acid is linoleic acid.

9. A process according to claim 1 wherein the fatty acid is constituted from linseed oil.

* * * * *